US006187836B1

(12) United States Patent
Oxman et al.

(10) Patent No.: US 6,187,836 B1
(45) Date of Patent: Feb. 13, 2001

(54) COMPOSITIONS FEATURING CATIONICALLY ACTIVE AND FREE RADICALLY ACTIVE FUNCTIONAL GROUPS, AND METHODS FOR POLYMERIZING SUCH COMPOSITIONS

(75) Inventors: Joel D. Oxman, Minneapolis; Matthew C. Trom, Cottage Grove, both of MN (US); Dwight W. Jacobs, Hudson, WI (US)

(73) Assignee: 3M Innovative Properties Company, St. Paul, MN (US)

( * ) Notice: Under 35 U.S.C. 154(b), the term of this patent shall be extended for 0 days.

(21) Appl. No.: 09/092,550

(22) Filed: Jun. 5, 1998

(51) Int. Cl.$^7$ ..................................................... C08F 2/48
(52) U.S. Cl. .................. 522/148; 522/908; 522/162; 522/169; 522/168; 522/170; 522/182; 522/183; 522/100; 522/31; 522/14; 522/15; 522/25; 523/109; 523/115; 523/116; 523/118; 523/300
(58) Field of Search ................................ 522/100, 31, 14, 522/15, 28, 148, 162, 168, 169, 170, 182, 183; 523/109, 300, 116, 115, 118

(56) References Cited

U.S. PATENT DOCUMENTS

| | | | |
|---|---|---|---|
| 4,071,424 | * 1/1978 | Dart et al. | 204/159.15 |
| 4,156,035 | * 5/1979 | Tsao et al. | 427/44 |
| 4,221,698 | 9/1980 | Lee, Jr. et al. | 260/42.52 |
| 4,228,062 | 10/1980 | Lee, Jr. et al. | 260/42.28 |
| 4,256,828 | * 3/1981 | Smith | 430/280 |
| 4,318,766 | 3/1982 | Smith | 156/330 |
| 4,428,807 | * 1/1984 | Lee et al. | 204/159.14 |
| 4,439,380 | * 3/1984 | Michl et al. | 264/16 |
| 4,694,029 | * 9/1987 | Land | 522/8 |
| 4,719,149 | 1/1988 | Aasen et al. | 428/473 |
| 4,735,632 | * 4/1988 | Oxman et al. | 51/295 |
| 4,751,138 | * 6/1988 | Tumey et al. | 428/323 |
| 4,771,112 | 9/1988 | Engelbrecht | 525/327.3 |
| 4,828,583 | * 5/1989 | Oxman et al. | 51/295 |
| 4,835,193 | * 5/1989 | Hayase et al. | 522/15 |
| 4,933,376 | * 6/1990 | Sasaki et al. | 522/14 |
| 4,985,340 | 1/1991 | Palazzotto et al. | 430/270 |
| 5,095,045 | 3/1992 | Winkel et al. | 523/115 |
| 5,256,170 | 10/1993 | Harmer et al. | 51/293 |
| 5,266,609 | 11/1993 | Hall et al. | 523/116 |
| 5,318,999 | 6/1994 | Mitra et al. | 522/57 |
| 5,321,053 | * 6/1994 | Hino et al. | 522/26 |
| 5,326,621 | * 7/1994 | Palazzotto et al. | 428/195 |
| 5,426,134 | 6/1995 | Rheinberger et al. | 523/118 |
| 5,453,450 | 9/1995 | Kinzer et al. | 522/18 |
| 5,472,991 | 12/1995 | Schmitt et al. | 522/4 |
| 5,545,676 | * 8/1996 | Palazzotto et al. | 522/15 |
| 5,571,297 | 11/1996 | Swei et al. | 51/298 |
| 5,599,622 | 2/1997 | Kinzer et al. | 428/355 |
| 5,624,976 | 4/1997 | Klee | 523/116 |
| 5,639,802 | * 6/1997 | Nekers | 522/25 |
| 5,658,963 | * 8/1997 | Qian et al. | 522/14 |
| 5,672,637 | 9/1997 | Mahoney et al. | 522/25 |
| 5,721,289 | 2/1998 | Karim et al. | 522/31 |
| 5,750,590 | * 5/1998 | Schaefer et al. | 523/111 |
| 5,856,373 | * 1/1999 | Kaisaki et al. | 522/25 |

FOREIGN PATENT DOCUMENTS

| | | |
|---|---|---|
| 34512/95 | 5/1996 | (AU) . |
| 2403211 | 7/1975 | (DE) . |
| 195 06 222 | * 2/1995 | (DE) . |
| 196 08 313 A1 | * 8/1997 | (DE) . |
| 0 330 117 | 8/1989 | (EP) . |
| 0 429 250 A2 | 5/1991 | (EP) . |
| 0 678 533 A2 | 10/1995 | (EP) . |
| 0 361 542 A1 | 8/1996 | (EP) . |
| 0 728 790 A1 | 8/1996 | (EP) . |
| 1 408 265 | * 10/1975 | (GB) . |
| 1-174523 | 7/1989 | (JP) . |
| 5-33250 | 5/1993 | (JP) . |
| 688193 | 9/1979 | (RU) . |
| 782200 | 9/1981 | (RU) . |
| 2057522 | 4/1996 | (RU) . |
| 95/14716 | * 6/1995 | (WO) . |
| 96/13538 | * 5/1996 | (WO) . |
| WO 96/13538 | 5/1996 | (WO) . |

OTHER PUBLICATIONS

Tang et al., "Study of Diisocyanate Modified EAM Resin for Orthodontics Adhesive", *Stomatol. Coll.*, 4th Mil. Med. Univ., Peopl. Rep. China, Huaxue Yu Nianhe, 4:208–11 (1992).

Moore et al., "Free Radical and Cationic Cure of Pigmented Coatings Using Visible Light Photoinitiators", Spectrum Group Ltd., p. 17–24.

Hans et al., "Photoinitiator Systems for Concurrent Radical and Cationic Polymerization", *Pure& Appl. Chem.*, 60(7):1033–1038 (1988).

Wang et al., "Photopolymerization of Glycidyl Acrylate and Glycidyl Methacrylate Investigated By Differential Photocalorimetry and FT–I.R.", *Eur. Polym. J.*, 29(10):1379–1386 (1993).

Lee et al., "Properties of a New Carvable Composite Dental Filling Material", *Australian Dental Journal*, 22(4):232–235 (1977).

Timpe et al., "Bivalent Initiators—Novel Systems for the Photopolymerization", *Sci. Journ. Techn. Univer. Leuna–Merseburg*, 26(3):439–448 (1984).

Phillips, "Composite Restorative Resins", *JADA* 80:357–358 (1970).

(List continued on next page.)

Primary Examiner—James J. Seidleck
Assistant Examiner—Sanza McClendon

(57) ABSTRACT

Photopolymerizable compositions that include free radically active and cationically active functional groups, and methods for polymerizing such compositions, in which the onset of cationic polymerization is controllably delayed to extend the time between formation of a moldable gel and formation of a hardened solid.

59 Claims, 2 Drawing Sheets

OTHER PUBLICATIONS

Derwent Abstract–ACC–NO 1973–2621 7U: Photopolymrizable composition. to Dart et al, Oct. 1975.*

Crivello et al. Journal of Polymer Science: Polymer Lettes Edition. vol. 17, 759–764, Jul. 1979.*

Yildrim et al. Polymer 40 (1999) 3885–3890, Sep. 1998.*

Crivello Cationic Polymerization—Iodonium and Sulfonium Salt Photoinitiators, Aug. 1983.*

Photopolymerization of Surface Coatings. Chapter 3: Photoinitiators and Photosensitizers.*

Hawley's Condensed Chemical Dictionary, 13th Ed. pp. 828.*

* cited by examiner

COMPOSITIONS FEATURING CATIONICALLY ACTIVE AND FREE RADICALLY ACTIVE FUNCTIONAL GROUPS, AND METHODS FOR POLYMERIZING SUCH COMPOSITIONS

BACKGROUND OF THE INVENTION

The invention relates to polymerizing compositions having cationically active and free radically active functional groups.

Acrylate and methacrylate-based compositions polymerize via a one-step free radical mechanism. "Hybrid" compositions featuring both cationically and free radically polymerizable components have been proposed as well. Epoxy resins are typically used as the cationically polymerizable component, and offer the advantage of reduced shrinkage relative to acrylate and methacrylate-based compositions. The hybrid composition polymerizes initially to form a moldable "gel" that can be shaped and compacted. As the polymerization proceeds, the gel forms a hard solid.

SUMMARY OF THE INVENTION

The inventors have discovered that one problem with hybrid compositions is that it is difficult to control the amount of time between formation of the gel and formation of the hardened solid. To address this problem, the inventors have discovered polymerizable hybrid compositions, and methods for polymerizing the free radically active and cationically active functional groups of such compositions, in which the onset of cationic polymerization can be controllably delayed to extend the time between formation of the moldable gel and formation of the hardened solid. The net result is enhanced processing flexibility.

Accordingly, in a first aspect, the invention features a photopolymerizable composition that includes: (a) a cationically active functional group; (b) a free radically active functional group; and (c) a photoinitiation system. Examples of preferred photopolymerizable compositions are dental compositions such as dental adhesives, dental composites (including dental restoratives and prostheses), and dental sealants.

The photoinitiation system is capable of initiating, at a reaction temperature less than about 40° C., free radical polymerization of the free radically active functional group after a finite induction period $T_1$ and cationic polymerization of the cationically active functional group after a finite induction period $T_3$, where $T_3$ is greater than $T_1$. $T_1$ and $T_3$ are measured relative to administration of the first dose of actinic radiation which occurs at $T_0$. The photoinitiation system includes: (i) a source of species capable of initiating free radical polymerization of the free radically active functional group and cationic polymerization of the cationically active functional group; and (ii) a cationic polymerization modifier. The amount and type of modifier are selected such that in the absence of the modifier, cationic polymerization of the cationically active functional group is initiated under the same irradiation conditions at the end of a finite induction period $T_2$ (also measured relative to $T_0$), where $T_2$ is less than $T_3$.

As used herein, a "cationically active functional group" refers to a chemical moiety that is activated in the presence of an initiator capable of initiating cationic polymerization such that it is available for reaction with other compounds bearing cationically active functional groups. A "free radically active functional group" refers to a chemical moiety that is activated in the presence of an initiator capable of initiating free radical polymerization such that it is available for reaction with other compounds bearing free radically active functional groups.

"Initiation of polymerization" after a "finite induction period" means that after a finite period of time has elapsed, an exotherm (as measured by differential scanning calorimetry) occurs, reflecting initiation of the polymerizable groups. Initiation (and thus a successful polymerization) of the cationically polymerizable groups is said to have occurred if the area under the resulting exotherm peak is greater than 5% of the area of the corresponding peak for a control composition lacking the modifier but irradiated under the same conditions set forth in the Examples, infra.

The term "composite" refers to a filled dental material. The term "restorative" refers to a composite which is polymerized after it is disposed adjacent to a tooth. The term "prosthesis" refers to a composite which is shaped and polymerized for its final use (e.g., as crown, bridge, veneer, inlay, onlay or the like) before it is disposed adjacent to a tooth. The term "sealant" refers to a lightly filled composite or to an unfilled dental material which is polymerized after it is disposed adjacent to a tooth. Each of these materials is suitable for temporary or permanent use.

Suitable components of the photopolymerizable composition include epoxy resins (which contain cationically active epoxy groups), vinyl ether resins (which contain cationically active vinyl ether groups), and ethylenically active unsaturated compounds (which contain free radically active unsaturated groups). Examples of useful ethylenically unsaturated compounds include acrylic acid esters, methacrylic acid esters, hydroxy-functional acrylic acid esters, hydroxy-functional methacrylic acid esters, and combinations thereof. Also suitable are polymerizable components that contain both a cationically active functional group and a free radically active functional group in a single molecule. Examples include epoxy-functional acrylic acid esters, methacrylic acid esters, and combinations thereof.

A preferred material for component (i) of the photoinitiation system is an onium salt, e.g., an iodonium salt. The photoinitiation system preferably contains a photosensitizer as well, e.g., a visible light sensitizer. The term "visible light" refers to light having a wavelength of about 400 to about 1000 nanometers. Examples of suitable photosensitizers include alpha diketones.

The cationic polymerization modifier is preferably selected such that the photoinitiator system has a photoinduced potential less than that of 3-dimethylaminobenzoic acid in a standard solution of $2.9 \times 10^{-5}$ moles/g diphenyliodonium hexafluoroantimonate and $1.5 \times 10^{-5}$ moles/g camphorquinone in 2-butanone. The modifiers typically are bases having $pk_b$ values, measured in aqueous solution, of no greater than 10. Particularly preferred are modifiers in which the type and amount of modifier are selected such that cationic polymerization of the cationically active functional group after a finite induction period $T_3$ proceeds at a rate that is greater than the rate in the absence of the cationic polymerization modifier under the same irradiation conditions.

Examples of suitable cationic polymerization modifiers include aromatic amines (e.g., t-butyldimethylaniline); aliphatic amines (e.g., trimethyl-1,3-propane diamine, 2-(methylamino)ethanol, and combinations thereof); aliphatic amides; aliphatic ureas; phosphines (e.g., aliphatic and aromatic); salts of organic or inorganic acids (e.g., sulfinic acid salts); and combinations thereof.

In a second aspect, the invention features a method of polymerizing a photopolymerizable composition that includes exposing the composition to a source of actinic radiation (preferably a source of visible radiation) at a reaction temperature sufficiently high to initiate the polymerization reaction. Preferably, the reaction temperature is less than 40° C. Suitable photopolymerizable compositions include the compositions described above. Also suitable are photopolymerizable compositions that include a cationically active functional group, free radically active functional group, and photoinitiation system (as defined above), but which are not necessarily capable of polymerizing at temperatures less than 40° C. The method is particularly useful for photopolymerizable compositions in the form of dental adhesives, dental composites, dental sealants, and combinations thereof, in which case the method includes applying the photopolymerizable composition to a surface and conducting, polymerization within the oral cavity at temperatures less than 40° C.

In one embodiment, the photopolymerizable composition is continuously exposed to actinic radiation beginning at $T_0$. In another embodiment, the photopolymerizable is exposed to a single dose of actinic radiation at $T_0$.

In a third embodiment, two separate irradiation events occur. First, the photopolymerizable composition is exposed at a first reaction temperature to a first dose of actinic radiation at $T_0$ to initiate polymerization of the free radically active functional group after a finite induction period $T_1$. Thereafter, the photopolymerizable composition is exposed at a second reaction temperature to a second dose of actinic radiation to initiate polymerization of the cationically active functional group after a finite induction period $T_3$ which is greater than $T_1$ (where both $T_1$ and $T_3$ are measured relative to $T_0$). Preferably, actinic radiation of the same wavelength is used for both irradiation events. The first and second reaction temperatures preferably are substantially the same.

In a third aspect, the invention features a method of preparing a polymerized dental composition in which the polymerizable composition includes two separate initiation systems. One of the initiation systems initiates polymerization of the free radically active functional group at a first reaction temperature less than 40° C. Suitable examples include photoinitiation systems, thermal initiation systems, and redox (i.e., autocure) initiation systems. The other initiation system is a photoinitiation system that initiates photopolymerization of the cationically active functional group at a second reaction temperature less than 40° C. The first and second reaction temperatures preferably are substantially the same.

The method includes applying the polymerizable composition to a surface, inducing polymerization of the free radically active functional group, and thereafter, in a separate step, exposing the composition to actinic radiation to cause polymerization of the cationically active functional group. Polymerization is conducted within the oral cavity.

The invention provides hybrid polymerizable compositions in which the onset of polymerization of the cationically active functional groups can be delayed relative to the onset of polymerization of the free radically active functional groups for a desired period of time without adversely affecting cationic polymerization once it is initiated at the end of that period. The invention thus provides flexibility and control in applications for which the compositions are used. These advantages are particularly useful in dental applications where the compositions may be applied within the oral cavity. By delaying polymerization of the cationically active component, the dentist has ample time to apply and shape the composition to conform to the contours of the oral surface to which it is applied, e.g., a tooth. Once these operations are complete, the dentist can then initiate the cationic polymerization to form the final, hardened material.

Other features and advantages of the invention will be apparent from the following description of the preferred embodiments thereof, and from the claims.

DETAILED DESCRIPTION

Polymerizable Composition

Figure 1:
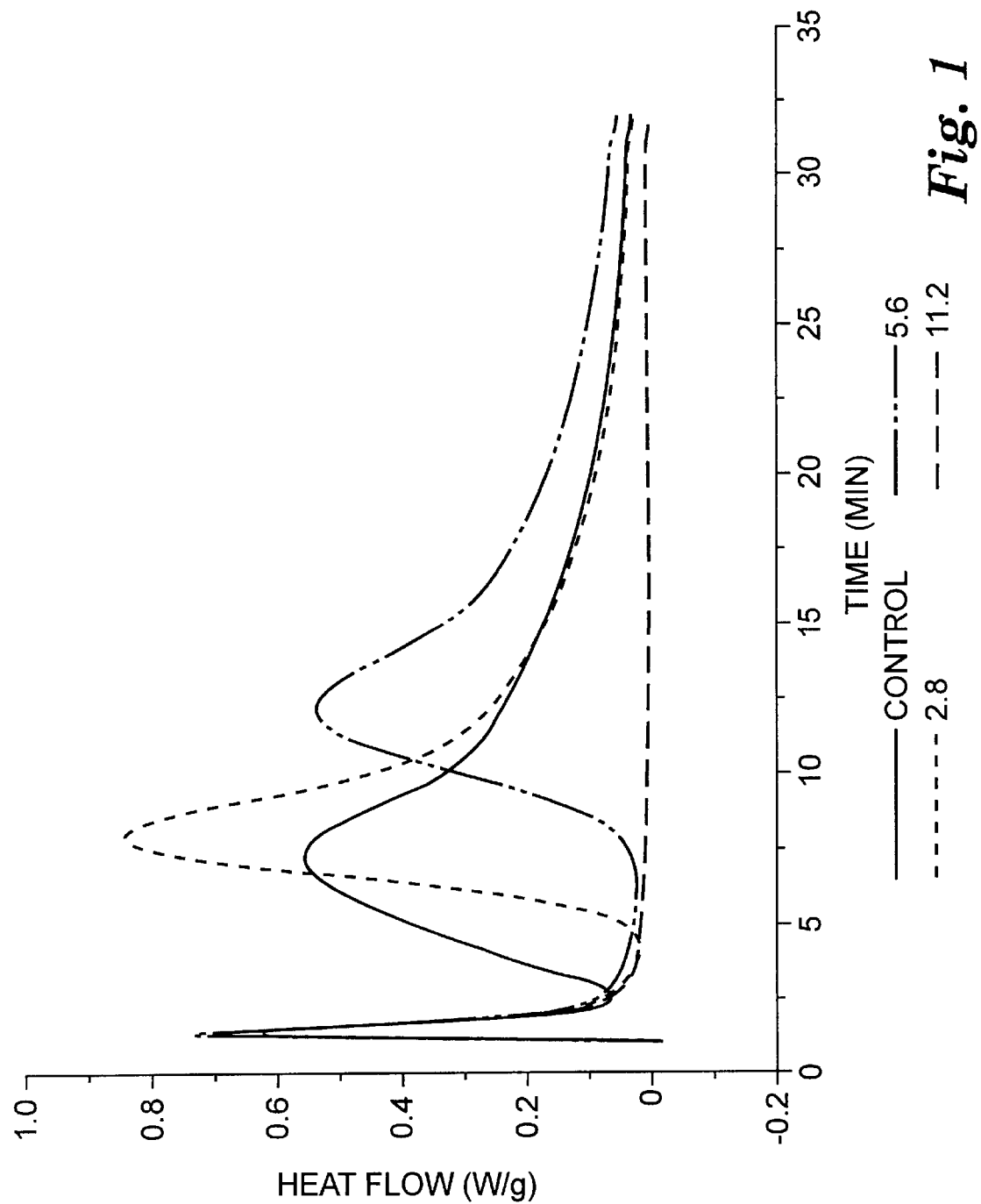
FIG. 1 is a plot of heat flow vs. time obtained by Photo Differential Scanning Calorimetry for polymerizable compositions containing various concentrations of the cationic polymerization modifier 2-(methylamino)-ethanol.

The polymerizable compositions of the invention feature one or more cationically active functional groups, one or more free radically active functional groups, and at least one initiation system. The compositions are designed for use in a staged polymerization process in which the free radically active functional groups are polymerized in a first step and the cationically active functional groups are polymerized thereafter in a second step. The initiation system may perform the dual function of initiating both cationic and free radical polymerization. Alternatively, two separate initiation systems, one of which initiates free radical polymerization and the other of which initiates cationic polymerization, may be used.

Single Initiation System

An initiation system suitable for initiating both free radical and cationic polymerization is designed such that for a given reaction temperature, photoinitiation of free radical polymerization occurs after a finite induction period $T_1$ and photoinitiation of cationic polymerization occurs after a finite induction period $T_3$, where $T_3$ is greater than $T_1$. $T_1$ and $T_3$ are measured relative to administration of the first dose of actinic radiation which begins at $T_0$. The photoinitiation system includes: (i) a source of species capable of initiating free radical polymerization of the free radically active functional group and cationic polymerization of the cationically active functional group; and (ii) a cationic polymerization modifier. The amount and type of modifier are selected such that in the absence of the modifier, initiation of cationic polymerization under the same irradiation conditions occurs at the end of a finite induction period $T_2$ (also measured relative to $T_0$), where $T_2$ is less than $T_3$.

The induction periods ($T_1$, $T_2$, and $T_3$) can be measured using differential scanning calorimetry. Following the first irradiation event at $T_0$, the exotherm of the reaction is measured as a function of time. Both initiation of free radical polymerization and initiation of cationic polymerization result in an exotherm, observed as a pair of separate peaks on a graph of heat flows vs. time. The time at which initiation occurs is taken to be the time at which the exotherm begins to increase.

There are numerous examples of sources of species capable of initiating both free radical and cationic polymerization. Representative examples include onium salts and mixed ligand arene cyclopentadienyl metal salts with complex metal halide ions, as described in "CRC Handbook of Organic Photochemistry", vol II, ed. J. C. Scaiano, pp. 335–339 (1989). Preferably, the source is an onium salt. Of the onium salts, iodonium salts (e.g., aryl iodonium salts) are particularly useful. The iodonium salt should be soluble in the composition and preferably is shelf-stable, meaning it does not spontaneously promote polymerization when dissolved therein in the presence of the cationic polymerization modifier and photosensitizer (if included). Accordingly, selection of a particular iodonium salt may depend to some extent upon the particular polymerizable reactants, cationic polymerization modifiers, and sensitizers (if present).

Suitable iodonium salts are described in U.S. Pat. Nos. 3,729,313; 3,741,769; 4,250,053; and 4,394,403, the iodonium salt disclosures of which are incorporated herein by reference. The iodonium salt can be a simple salt, containing an anion such as $Cl^-$, $Br^-$, $I^-$, $C_4H_5SO_3^-$, or $C(SO_2CF_3)_3^-$; or a metal complex salt containing an antimonate, arsenate, phosphate, or borate such as $SbF_5OH^-$, $AsF_6^-$, or $B(C_6F_5)_4^-$. Mixtures of iodonium salts can be used if desired.

Examples of useful aromatic iodonium complex salt photoinitiators include: diphenyliodonium tetrafluoroborate; di(4-methylphenyl)iodonium tetrafluoroborate; phenyl-4-methylphenyliodonium tetrafluoroborate; di(4-heptylphenyl)iodonium tetrafluoroborate; di(3-nitrophenyl)iodonium hexafluorophosphate; di(4-chlorophenyl)iodonium hexafluorophosphate; di(naphthyl)iodonium tetrafluoroborate; di(4-trifluoromethylphenyl)iodonium tetrafluoroborate; diphenyliodonium hexafluorophosphate; di(4-methylphenyl)iodonium hexafluorophosphate; diphenyliodonium hexafluoroarsenate; di(4-phenoxyphenyl)iodonium tetrafluoroborate; phenyl-2-thienyliodonium hexafluorophosphate; 3,5-dimethylpyrazolyl-4-phenyliodonium hexafluorophosphate; diphenyliodonium hexafluoroantimonate; 2,2'-diphenyliodonium tetrafluoroborate; di(2,4-dichlorophenyl)iodonium hexafluorophosphate; di(4-bromophenyl)iodonium hexafluorophosphate; di(4-methoxyphenyl)iodonium hexafluorophosphate; di(3-carboxyphenyl)iodonium hexafluorophosphate; di(3-methoxycarbonylphenyl)iodonium hexafluorophosphate, di(3-methoxysulfonylphenyl)iodonium hexafluorophosphate; di(4-acetamidophenyl)iodonium hexafluorophosphate; di(2-benzothienyl)iodonium hexafluorophosphate; diphenyliodonium hexafluoroantimonate; diphenyl or diaryliodonium tris-trifluoromethylsulfonyl methide; or diphenyl or diaryliodonium tetra(pentafluorophenyl)borate.

The cationic polymerization modifier preferably has a photoinduced potential less than that of 3-dimethylaminobenzoic acid in a standard solution of $2.9 \times 10^{-5}$ moles/g diphenyliodonium hexafluoroantimonate and $1.5 \times 10^{-5}$ moles/g camphorquinone in 2-butanone. The photoinduced potential can be evaluated in the following manner. A standard solution is prepared that contains $2.9 \times 10^{-5}$ moles/g of diphenyliodonium hexafluoroantimonate and $1.5 \times 10^{-5}$ moles/g of camphorquinone in 2-butanone. A pH electrode is then immersed in the solution and a pH meter is calibrated to zero mV. A test solution of the standard solution and the modifier is prepared next using the modifier at a concentration of $2.9 \times 10^{-5}$ moles/g. This test solution is irradiated using blue light having a wavelength of about 400 to 500 nm having an intensity of about 200 to 400 mW/cm² for about 5 to 10 seconds at a distance of about 1 mm. Millivolts relative to the standard solution are then determined by immersing the pH electrode in the test solution and obtaining a mV reading on the pH meter. Useful modifier are those compounds that provide a reading no greater than about 75 mV relative to the standard solution.

In some instances there may be some uncertainty regarding the outcome of the above procedure. This may be due to questions or uncertainty arising from the instrumentation employed, from the way the procedure was carried out, or other factors, or one may wish to verify the suitability of a particular modifier. A second test may be performed to verify the result obtained by following the above procedure and resolve any such uncertainty.

The second method involves the evaluation of the photoinduced potential of an initiator system that includes the modifier compared to a system that includes 3-dimethylamino benzoic acid. For this method, a standard solution of $2.9 \times 10^{-5}$ moles/g diphenyliodonium hexafluoroantimonate, $1.5 \times 10^{-5}$ moles/g camphorquinone and $2.9 \times 10^{-5}$ moles/g of 3-dimethylaminobenzoic acid in 2-butanone is prepared. A pH electrode is then immersed in the solution and a pH meter is calibrated to zero mV. The standard solution is irradiated with blue light having a wavelength of between about 400–500 nm and an intensity of about 200 to 400 mW/cm² for about 5 to 10 seconds using a focused light source such as a dental curing light at a distance of about 1 mm. After light exposure, the potential of the solution is measured by immersing a pH electrode in the irradiated standard solution and reading the potential in mV using a pH meter. A test solution is then prepared using $2.9 \times 10^{-5}$ moles/g of diphenyliodonium hexafluoroantimonate, $1.5 \times 10^{-5}$ moles/g of camphorquinone and $2.9 \times 10^{-5}$ moles/g of the modifier in 2-butanone. The test solution is irradiated and the photoinduced potential measured using the same technique as described for the standard solution. If the test solution has a photoinduced potential that is less than that of the 3-dimethylaminobenzoic acid containing standard solution, then the modifier may be a useful cationic polymerization modifier.

Useful cationic polymerization modifiers are typically bases having $pK_b$ values, measured in aqueous solution, of less than 10. Examples of classes of suitable cationic polymerization modifiers include aromatic amines, aliphatic amines, aliphatic amides, aliphatic ureas; aliphatic and aromatic phosphines, and salts of organic or inorganic acids (e.g., salts of sulfinic acid). Specific examples include 4-(dimethylamino)phenylacetic acid, dimethylaminophenethanol, dihydroxy p-toluidine, N-(3,5-dimethylphenyl)-N,N-diethanolamine, 2,4,6-pentamethylaniline, dimethylbenzylamine, N,N-dimethylacetamide, tetramethylurea, N-methyldiethanolamine, triethylamine, 2-(methylamino) ethanol, dibutylamine, diethanolamine, N-ethylmorpholine, trimethyl-1,3-propanediamine, 3-quinuclidinol, triphenylphosphine, sodium toluene sulfinate, tricyclohexylphosphine, N-methylpyrollidone, and t-butyldimethylaniline. These modifiers may be used alone or in combination with each other, or with a material having photoinduced potential greater than that of 3-dimethylaminobenzoic acid in a standard solution of $2.9 \times 10^{-5}$ moles/g diphenyliodonium hexafluoroantimonate and $1.5 \times 10^{-5}$ moles/g camphorquinone in 2-butanone; an example of such a material is ethyl 4-(dimethylamino) benzoate ("EDMAB").

The choice of modifier, and amount thereof, is selected based upon the photopolymerizable composition and the extent to which it is desired to delay initiation of the cationically polymerizable groups (i.e., what the target $T_3$ value is). In addition, it is important that the amount of modifier not be so high that polymerization is inhibited completely. As discussed in the Summary of the Invention, above, a successful cationic polymerization is one in which the area under the exotherm peak accompanying cationic initiation, as measured by differential scanning calorimetry, is greater than 5% of the area of the corresponding peak for a control composition lacking the modifier but irradiated under the same conditions set forth in the Examples, infra.

Another variable which influences whether or not successful polymerization occurs is the reaction temperature. For example, some compositions which do not successfully polymerize (as defined above) at one reaction temperature may successfully polymerize at a higher temperature. In general, however, it is preferred that the polymerization reaction be capable of proceeding at temperatures less than 40° C. This feature is particularly useful in the case of dental compositions where polymerization takes place within the oral cavity in which the temperature is at or slightly above body temperature (37° C.). If the composition is capable of polymerizing at reaction temperatures less than 40° C., the polymerization reaction can be conducted without supplying additional heat.

The inventors have discovered that one class of cationic polymerization modifiers offers an additional advantage. Specifically, these modifiers not only delay the onset of cationic polymerization, but, upon initiation, increase the rate of polymerization relative to the rate of polymerization in the absence of the cationic polymerization modifier conducted under the same irradiation conditions. The rate is measured using differential scanning calorimetry as the difference between the time required to reach maximum exotherm peak height ($T_4$) and the time at which polymerization is initiated (i.e., the induction time). Examples of modifiers found to exhibit this behavior include aliphatic amines such as N-methyldiethanolamine, triethylamine, dibutylamine, diethanolamine, N-ethylmorpholine, 2-(methylamino)ethanol, and dimethylbenzylamine.

The initiation system may also include a sensitizer such as a visible light sensitizer that is soluble in the polymerizable composition. The sensitizer preferably is capable of absorbing light having wavelengths in the range from about 300 to about 1000 nanometers.

Examples of suitable sensitizers include ketones, coumarin dyes (e.g., ketocoumarins), xanthene dyes, acridine dyes, thiazole dyes, thiazine dyes, oxazine dyes, azine dyes, aminoketone dyes, porphyrins, aromatic polycyclic hydrocarbons, p-substituted aminostyryl ketone compounds, aminotriaryl methanes, merocyanines, squarylium dyes, and pyridinium dyes. Ketones (e.g., monoketones or alpha-diketones), ketocoumarins, aminoarylketones, and p-substituted aminostyryl ketone compounds are preferred sensitizers. For applications requiring deep cure (e.g., cure of highly filled composites), it is preferred to, employ sensitizers having an extinction coefficient below about 1000 lmole$^{-1}$cm$^{-1}$, more preferably about or below 100 lmole$^{-1}$ cm$^{-1}$, at the desired wavelength of irradiation for photopolymerization. The alpha-diketones are an example of a class of sensitizers having this property, and are particularly preferred for dental applications.

Examples of particularly preferred visible light sensitizers include camphorquinone; glyoxal; biacetyl; 3,3,6,6-tetramethylcyclohexanedione; 3,3,7,7-tetramethyl-1,2-cycloheptanedione; 3,3,8,8-tetramethyl-1,2-cyclooctanedione; 3,3,18,18-tetramethyl- 1,2-cyclooctadecanedione; dipivaloyl; benzil; furil; hydroxybenzil; 2,3-butanedione; 2,3-pentanedione; 2,3-hexanedione; 3,4-hexanedione; 2,3-heptanedione; 3,4-heptanedione; 2,3-octanedione; 4,5-octanedione; and 1,2-cyclohexanedione; Of these, camphorquinone is the most preferred sensitizer.

Dual Initiation Systems

Staged polymerizations may also be effected using one initiation system for free radical polymerization and a separate initiation system for cationic polymerization. The free radical polymerization initiation system is selected such that upon activation, only free radical polymerization is initiated.

One class of initiators capable of initiating polymerization of free radically active functional groups, but not cationically active functional groups, includes conventional chemical initiator systems such as a combination of a peroxide and an amine. These initiators, which rely upon a thermal redox reaction, are often referred to as "auto-cure catalysts." They are typically supplied as two-part systems in which the reactants are stored apart from each other and then combined immediately prior to use.

A second class of initiators capable of initiating polymerization of free radically active functional groups, but not cationically active functional groups, includes free radical-generating photoinitiators, optionally combined with a photosensitizer or accelerator. Such initiators typically are capable of generating free radicals for addition polymerization at some wavelength between 200 and 800 nm. Examples include alpha-diketones, monoketals of alpha-diketones or ketoaldehydes, acyloins and their corresponding ethers, chromophore-substituted halomethyl-s-triazines, and chromophore-substituted halomethyl-oxadiazoles.

A third class of initiators capable of initiating polymerization of free radically active functional groups, but not cationically active functional groups, includes free radical-generating thermal initiators. Examples include peroxides and azo compounds such as AIBN.

The dual initiation systems further include a separate photoinitiation system for initiating polymerization of the cationically active functional groups. The cationic initiation system is selected such that activation of the free radical initiation system does not activate the cationic initiation system. Examples of suitable cationic photoinitiation systems for a dual initiation system composition include the onium salts and mixed ligand arene cyclopentadienyl metal salts with complex metal halide ions described above.

Polymerizable Components

The polymerizable compositions include cationically active functional groups and free radically active functional groups. Materials having cationically active functional groups include cationically polymerizable epoxy resins. Such materials are organic compounds having an oxirane ring, i.e., a group of the formula

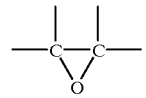

Which is polymerizable by ring opening. These materials include monomeric epoxy compounds and epoxides of the polymeric type and can be aliphatic, cycloaliphatic, aromatic or heterocyclic. These materials generally have, on the average, at least 1 polymerizable epoxy group per molecule, preferably at least about 1.5 and more preferably at least about 2 polymerizable epoxy groups per molecule. The polymeric epoxides include linear polymers having terminal epoxy groups (e.g., a diglycidyl ether of a polyoxyalkylene glycol), polymers having skeletal oxirane units (e.g., polybutadiene polyepoxide), and polymers having pendent epoxy groups (e.g., a glycidyl methacrylate polymer or copolymer). The epoxides may be pure compounds or may be mixtures of compounds containing one, two, or more epoxy groups per molecule. The "average" number of epoxy groups per molecule is determined by dividing the total number of epoxy groups in the epoxy-containing material by the total number of epoxy-containing molecules present.

These epoxy-containing materials may vary from low molecular weight monomeric materials to high molecular weight polymers and may vary greatly in the nature of their backbone and substituent groups. Illustrative of permissible substituent groups include halogens, ester groups, ethers, sulfonate groups, siloxane groups, nitro groups, phosphate groups, and the like. The molecular weight of the epoxy-containing materials may vary from about 58 to about 100,000 or more.

Useful epoxy-containing materials include those which contain cyclohexane oxide groups such as epoxycyclohexanecarboxylates, typified by 3,4-epoxycyclohexylmethyl-3,4-epoxycyclohexanecarboxylate, 3,4 -epoxy-2-methylcyclohexylmethyl-3,4-epoxy-2-methylcyclohexane carboxylate, and bis(3,4-epoxy-6-methylcyclohexylmethyl) adipate. For a more detailed list of useful epoxides of this nature, reference is made to the U.S. Pat. No. 3,117,099, which is incorporated herein by reference.

Further epoxy-containing materials which are useful in the compositions of this invention include glycidyl ether monomers of the formula

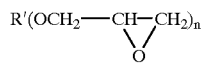

where R' is alkyl or aryl and n is an integer of 1 to 6. Examples are glycidyl ethers of polyhydric phenols obtained by reacting a polyhydric phenol with an excess of chlorohydrin such as epichlorohydrin (e.g., the diglycidyl ether of 2,2-bis-(2,3-epoxypropoxyphenol)-propane). Further examples of epoxides of this type are -described in U.S. Pat. No. 3,018,262, which is incorporated herein by reference, and in "Handbook of Epoxy Resins" by Lee and Neville, McGraw-Hill Book Co., New York (1967).

There are a host of commercially available epoxy resins which can be used in this invention. In particular, epoxides which are readily available include octadecylene oxide, epichlorohydrin, styrene oxide, vinylcyclohexene oxide, glycidol, glycidyl methacrylate, diglycidyl ether of Bisphenol A (e.g., those available under the trade designations "Epon 828", "Epon 825", "Epon 1004" and "Epon 1010" from Shell Chemical Co., "DER-331", "DER-332", and "DER-334", from Dow Chemical Co.), vinylcyclohexene dioxide (e.g., "ERL-4206" from Union Carbide Corp.), 3,4-epoxycyclohexylmethyl-3,4-epoxycyclohexene carboxylate (e.g., "ERL-4221" or "CYRACURE UVR 6110" or "UVR 6105" from Union Carbide Corp.), 3,4-epoxy-6-methylcyclohexylmethyl-3,4-epoxy-6-methyl-cyclohexene carboxylate (e.g., "ERL-4201" from Union Carbide Corp.), bis(3,4-epoxy-6-methylcyclohexylmethyl) adipate (e.g., "ERL-4289" from Union Carbide Corp.), bis(2,3-epoxycyclopentyl) ether (e.g., "ERL-0400" from Union Carbide Corp.), aliphatic epoxy modified from polypropylene glycol (e.g., "ERL-4050" and "ERL-4052" from Union Carbide Corp.), dipentene dioxide (e.g., "ERL-4269" from Union Carbide Corp.), epoxidized polybutadiene (e.g., "Oxiron 2001" from FMC Corp.), silicone resin containing epoxy functionality, flame retardant epoxy resins (e.g., "DER-580" a brominated bisphenol type epoxy resin available from Dow Chemical Co.), 1,4-butanediol diglycidyl ether of phenolformaldehyde novolak (e.g., "DEN-431" and "DEN-438" from Dow Chemical Co.), and resorcinol diglycidyl ether (e.g., "Kopoxite" from Koppers Company, Inc.), bis(3,4-epoxycyclohexyl)adipate (e.g., "ERL-4299" or "UVR-6128", from Union Carbide Corp.), 2-(3,4-epoxycyclohexyl-5, 5-spiro-3,4-epoxy) cyclohexane-meta-dioxane (e.g., "ERL-4234" from Union Carbide Corp.), vinylcyclohexene monoxide 1,2-epoxyhexadecane (e.g., "UVR-6216" from Union Carbide Corp.), alkyl glycidyl ethers such as alkyl $C_8$–$C_{10}$ glycidyl ether (e.g., "HELOXY Modifier 7" from Shell Chemical Co.), alkyl $C_{12}$–$C_{14}$ glycidyl ether (e.g., "HELOXY Modifier 8" from Shell Chemical Co.), butyl glycidyl ether (e.g., "HELOXY Modifier 61" from Shell Chemical Co.), cresyl glycidyl ether (e.g., "HELOXY Modifier 62" from Shell Chemical Co.), p-ter butylphenyl glycidyl ether (e.g., "HELOXY Modifier 65" from Shell Chemical Co.), polyfunctional glycidyl ethers such as diglycidyl ether of 1,4-butanediol (e.g., "HELOXY Modifier 67" from Shell Chemical Co.), diglycidyl ether of neopentyl glycol (e.g., "HELOXY Modifier 68" from Shell Chemical Co.), diglycidyl ether of cyclohexanedimethanol (e.g., "HELOXY Modifier 107" from Shell Chemical Co.), trimethylol ethane triglycidyl ether (e.g., "HELOXY Modifier 44" from Shell Chemical Co.), trimethylol propane triglycidyl ether (e.g., "HELOXY Modifier 48" from Shell Chemical Co.), polyglycidyl ether of an aliphatic polyol (e.g., "HELOXY Modifier 84" from Shell Chemical Co.), polyglycol diepoxide (e.g., "HELOXY Modifier 32" from Shell Chemical Co.), bisphenol F epoxides (e.g., "EPN-1138" or "GY-281" from Ciba-Geigy Corp.), 9,9-bis[4-(2, 3-epoxypropoxy)-phenyl]fluorenone (e.g., "Epon 1079" from Shell Chemical Co.).

Still other epoxy resins contain copolymers of acrylic acid esters or glycidol such as glycidylacrylate and glycidylmethacrylate with one or more copolymerizable vinyl compounds. Examples of such copolymers are 1:1 styrene-glycidylmethacrylate, 1:1 methylmethacrylate-glycidylacrylate and a 62.5:24:13.5 methylmethacrylate-ethyl acrylate-glycidylmethacrylate.

Other useful epoxy resins are well known and contain such epoxides as epichlorohydrins, alkylene oxides, e.g., propylene oxide, styrene oxide; alkenyl oxides, e.g., butadiene oxide; glycidyl esters, e.g., ethyl glycidate.

Blends of various epoxy-containing materials are also contemplated. Examples of such blends include two or more weight average molecular weight distributions of epoxy-containing compounds, such as low molecular weight (below 200), intermediate molecular weight (about 200 to 10,000) and higher molecular weight (above about 10,000). Alternatively or additionally, the epoxy resin may contain a blend of epoxy-containing materials having different chemical natures, such as aliphatic and aromatic, or functionalities, such as polar and non-polar.

Other types of useful materials having cationically active functional groups include vinyl ethers, oxetanes, spiro-orthocarbonates, spiro-orthoesters, and the like.

Materials having free radically active functional groups include monomers, oligomers, and polymers having one or more ethylenically unsaturated groups. Suitable materials contain at least one ethylenically unsaturated bond, and are capable of undergoing addition polymerization. Such free radically polymerizable materials include mono-, di- or poly- acrylates and methacrylates such as methyl acrylate, methyl methacrylate, ethyl acrylate, isopropyl methacrylate, n-hexyl acrylate, stearyl acrylate, allyl acrylate, glycerol diacrylate, glycerol triacrylate, ethyleneglycol diacrylate, diethyleneglycol diacrylate, triethyleneglycol dimethacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexacrylate, bis[1-(2-acryloxy)]-p-ethoxyphenyldimethylmethane, bis[1-(3-acryloxy-2-hydroxy)]-p-propoxyphenyldimethylmethane, and trishydroxyethyl-isocyanurate trimethacrylate; the bis-acrylates and bis-methacrylates of polyethylene glycols of molecular weight 200–500, copolymerizable mixtures of acrylated monomers such as those in U.S. Pat. No. 4,652,274, and acrylated oligomers such as those of U.S. Pat. No. 4,642,126; and vinyl compounds such as styrene, diallyl phthalate, divinyl succinate, divinyl adipate and divinylphthalate. Mixtures of two or more of these free radically polymerizable materials can be used if desired.

If desired, both cationically active and free radically active functional groups may be contained in a single molecule. Such molecules may be obtained, for example, by reacting a di- or poly-epoxide with one or more equivalents of an ethylenically unsaturated carboxylic acid. An example of such a material is the reaction product of UVR-6105 (available from Union Carbide) with one equivalent of methacrylic acid. Commercially available materials having epoxy and free-radically active functionalities include the "Cyclomer" series, such as Cyclomer M-100, M-101, or A-200 available from Daicel Chemical, Japan, and Ebecryl-3605 available from Radcure Specialties.

Other Additives

The polymerizable composition may further include a hydroxyl-containing material. Suitable hydroxyl-containing materials can be any organic material having hydroxyl functionality of at least 1, and preferably at least 2. Preferably, the hydroxyl-containing material contains two or more primary or secondary aliphatic hydroxyl groups (i.e., the hydroxyl group is bonded directly to a non-aromatic carbon atom). The hydroxyl groups can be terminally situated, or they can be pendent from a polymer or copolymer. The molecular weight of the hydroxyl-containing organic material can vary from very low (e.g., 32) to very high (e.g., one million or more). Suitable hydroxyl-containing materials can have low molecular weights, i.e. from about 32 to 200, intermediate molecular weight, i.e. from about 200 to 10,000, or high molecular weight, i.e. above about 10,000. As used herein, all molecular weights are weight average molecular weights.

The hydroxyl-containing materials can be non-aromatic in nature or can contain aromatic functionality. The hydroxyl-containing material can optionally contain heteroatoms in the backbone of the molecule, such as nitrogen, oxygen, sulfur, and the like. The hydroxyl-containing material can, for example, be selected from naturally occurring or synthetically prepared cellulosic materials. Of course, the hydroxyl-containing material is also substantially free of groups which may be thermally or photolytically unstable; that is, the material will not decompose or liberate volatile components at temperatures below about 100° C. or in the presence of actinic light which may be encountered during the desired polymerization conditions for the free radically active components of the polymerizable composition.

Representative examples of suitable hydroxyl-containing materials having a hydroxyl functionality of 1 include alkanols, monoalkyl ethers of polyoxyalkyleneglycols, monoalkyl ethers of alkylene-glycols, and others known in the art.

Representative examples of useful monomeric polyhydroxy organic materials include alkylene glycols (e.g., 1,2-ethanediol; 1,3-propanediol; 1,4-butanediol; 1,6-hexanediol; 1,8-octanediol; 2-ethyl-1,6-hexanediol; bis(hydroxymethyl)cyclohexane; 1,18-dihydroxyoctadecane; 3-chloro-1,2-propanediol); polyhydroxyalkanes (e.g., glycerine, tri-methylolethane, pentaerythritol, sorbitol) and other polyhydroxy compounds; 2-butyne-1,4-diol; 4,4-bis(hydroxymethyl)diphenylsulfone; castor oil; and the like.

Representative examples of useful polymeric hydroxyl-containing materials include polyoxyethylene and polyoxypropylene glycols, and particularly the polyoxyethylene and polyoxypropylene glycol diols and triols having molecular weights from about 200 to about 10,000 corresponding to a hydroxy equivalent weight of 100 to 5000 for the diols or 70 to 3300 for triols; polytetramethylene ether glycols such as polytetrahydrofuran or "poly THF" of varying molecular weight; copolymers of hydroxypropyl and hydroxyethyl acrylates and methacrylates with other free radical-polymerizable monomers such as acrylate esters, vinyl halides, or styrene; copolymers containing pendent hydroxy groups formed by hydrolysis or partial hydrolysis of vinyl acetate copolymers, polyvinylacetal resins containing pendent hydroxyl groups; modified cellulose polymers such as hydroxyethylated and hydroxypropylated cellulose; hydroxy-terminated polyesters; hydroxy-terminated polylactones, and particularly the polycaprolactones; fluorinated polyoxyethylene or polyoxypropylene glycols; and hydroxy-terminated polyalkadienes.

Useful commercially available hydroxyl-containing materials include the "TERATHANE" series of polytetramethylene ether glycols such as "TERATHANE" 650, 1000, 2000 and 2900 (available from du Pont de Nemours, Wilmington, Del.) the "PEP" series of polyoxyalkylene tetrols having secondary hydroxyl groups such as "PEP" 450, 550 and 650; "BUTVAR" series of polyvinylacetal resins such as "BUTVAR" B-72A, B-73, B-76, B-90 and B-98 (available from Monsanto Chemical Company, St. Louis, Mo.); and the "FORMVAR" series of resins such as 7/70, 12/85, 7/95S, 7/95E, 15/95S and 15/95E (available from Monsanto Chemical Company); the "TONE" series of polycaprolactone polyols such as "TONE" 0200, 0210, 0230,0240, 0300 and 0301 (available from Union Carbide); "PARAPLEX U-148" aliphatic polyester diol (available from Rohm and Haas, Philadelphia, Pa.), the "MULTRON" R series of saturated polyester polyols such as "MULTRON" R-2, R-12A, R- 16, R-18, R-38, R-68 and R-74 (available from Mobay Chemical Co.); "KLUCEL E" hydroxypropylated cellulose having an equivalent weight of approximately 100 (available from Hercules Inc.); "Alcohol Soluble Butyrate" cellulose acetate butyrate ester having a hydroxyl equivalent weight of approximately 400 (available from Eastman Kodak Co., Rochester, N.Y.); polyether polyols such as polypropylene glycol diol (e.g., "ARCOL PPG-425", "Arcol PPG-725", "ARCOL PPG-1025", "ARCOL PPG-2025", ARCOL PPG-3025", "ARCOL PPG-4025" from ARCO Chemical Co.); polypropylene glycol triol (e.g., "ARCOL LT-28", "ARCOL LHT-42", "ARCOL LHT 112", "ARCOL LHT 240" "ARCOL LG-56", "ARCOL LG-168", "ARCOL LG-650" from ARCO Chemical Co.); ethylene oxide capped polyoxypropylene triol or diol (e.g., "ARCOL 11–27", "ARCOL 11–34", "ARCOL E-351", "ARCOL E-452", "ARCOL E-785", "ARCOL E-786" from ARCO Chemical Co.); ethoxylated bis-phenol A; propylene oxide or ethylene oxide—based polyols (e.g., "VORANOL" polyether polyols from the Dow Chemical Co.).

The amount of hydroxyl-containing organic material used in the polymerizable compositions may vary over broad ranges, depending upon factors such as the compatibility of the hydroxyl-containing material with the epoxide and/or free radically polymerizable component, the equivalent weight and functionality of the hydroxyl-containing material, the physical properties desired in the final composition, the desired speed of polymerization, and the like.

Blends of various hydroxyl-containing materials may also be used. Examples of such blends include two or more molecular weight distributions of hydroxyl-containing compounds, such as low molecular weight (below 200), intermediate molecular weight (about 200 to 10,000) and higher molecular weight (above about 10,000). Alternatively, or additionally, the hydroxyl-containing material can contain a blend of hydroxyl-containing materials having different chemical natures, such as aliphatic and aromatic, or functionalities, such as polar and non-polar. As an additional example, one may use mixtures of two or more poly-functional hydroxy materials or one or more monofunctional hydroxy materials with poly-functional hydroxy materials.

The polymerizable material(s) can also contain hydroxyl groups and free radically active functional groups in a single molecule. Examples of such materials include hydroxyalkylacrylates and hydroxyalkylmethacrylates such as hydroxyethylacrylate, hydroxyethylmethacrylate; glycerol mono- or di-(meth)acrylate; trimethylolpropane mono- or di-(meth)acrylate, pentaerythritol mono-, di-, and tri-(meth)acrylate, sorbitol mono-, di-, tri-, tetra-, or penta-(meth)acrylate; and 2,2-bis[4-(2-hydroxy-3-methacryloxypropoxy)phenyl]propane.

The polymerizable material(s) can also contain hydroxyl groups and cationically active functional groups in a single molecule. An example is a single molecule that includes both hydroxyl groups and epoxy groups.

The polymerizable composition can also contain suitable additives such as fluoride sources, anti-microbial agents, accelerators, stabilizers, absorbers, pigments, dyes, viscosity modifiers, surface tension depressants and wetting aids, antioxidants, fillers, and other ingredients well known to those skilled in the art. The amounts and types of each ingredient should be adjusted to provide the desired physical and handling properties before and after polymerization.

Polymerization Procedure

The polymerizable compositions are prepared by admixing, under "safe light" conditions, the various components of the compositions. Suitable inert solvents may be employed if desired when effecting the mixture. Examples of suitable solvents include acetone, dichloromethane, and acetonitrile.

In the case of single initiation systems, polymerization is effected by exposing the composition to a radiation source, preferably a visible light source. It is convenient to employ light sources that emit ultraviolet or visible light such as quartz halogen lamps, tungsten-halogen lamps, mercury arcs, carbon arcs, low-, medium-, and high-pressure mercury lamps, plasma arcs, light emitting diodes, and lasers.

In general, useful light sources have intensities in the range of 200–500 mW/cm$^2$. One example, which is particularly useful for dental applications, is a Visilux dental curing light commercially available from 3M Company of St. Paul, Minn. Such lights have an intensity of about 200–400 mW/cm$^2$ at a wavelength of 400–500 nm.

The exposure may be effected in several ways. For example, the polymerizable composition may be continuously exposed to radiation throughout the entire polymerization process. It is also possible to expose the composition to a single dose of radiation, and then remove the radiation source, thereby allowing polymerization to occur. Preferably, however, the composition is initially exposed to a single dose of radiation to initiate polymerization of the free radically active functional groups, followed by exposure to a second dose of radiation to initiate polymerization of the cationically active functional groups.

Where dual exposures are employed, the intensity of each dosage may be the same or different. Similarly, the total energy of each exposure may be the same or different.

Regardless of the particular irradiation protocol employed, cationic polymerization-initiating species are also generated during the first exposure. However, the amount of cationic polymerization modifier is sufficient to scavenge some or all of these species, thereby preventing cationic polymerization from occurring until a desired amount of time has elapsed.

In the case of a single dose exposure, the amount of modifier is adjusted so that a sufficient number of cationic polymerization-initiating species remains to initiate cationic polymerization. Initiation is delayed, however, because the concentration of cationic polymerization-initiating species effectively has been decreased.

In the case of continuous radiation exposure, additional cationic polymerization-initiating species continue to be generated, thereby augmenting the concentration of such species. Again, however, because of the cationic scavenging effect of the modifier, the concentration of such species is lower than it would have been in the absence of the modifier, resulting in delayed cationic polymerization.

In the case of the dual exposure protocol, the modifier concentration is adjusted such that it scavenges substantially all of the available cationic polymerization-initiating species, thereby preventing any significant amount of cationic polymerization from occurring. Upon exposure to a second dose of radiation, however, additional species are generated. Because modifier molecules are no longer available to perform the scavenging function, these species then proceed to initiate cationic polymerization. The net effect, therefore, is to "turn off" cationic polymerization until a desired amount of time has elapsed and then to "turn it on" again at the end of this period.

Delaying the onset of cationic polymerization is also achieved using the dual initiation systems. In such systems, preferential polymerization of the free radically active functional groups is initiated by selectively activating the free radical initiation system. Because this system does not generate cationically active species, cationic polymerization does not occur. After a desired amount of time has elapsed, cationic polymerization is activated by exposing the composition to radiation (preferably visible radiation), at which point the cationic polymerization proceeds.

Regardless of whether single or dual initiation systems are used, the ability to perform a staged cure offers the advantage of controlling the overall polymerization process. This ability is particularly useful in dentistry, as the viscosity (and thus the workability) of the composition changes significantly throughout the polymerization process. For example, the pre-polymerized composition is generally in the form of a viscous liquid that can readily be applied to a tooth. Upon irradiation, polymerization of the free radically active groups occurs, leading to the ultimate formation of a higher viscosity "gel." This gel has unique handling characteristics. Specifically, it can be readily shaped, adapted, carved, or otherwise manipulated; thus, the dentist can manipulate it to fill crevices and conform to desired portions of the tooth surface. Once manipulation is complete, cationic polymerization is initiated, causing the composition to form a hardened solid that provides the ultimate characteristics of the product. This solid, however, cannot be readily manipulated without using mechanical abrasives or machining (e.g., burrs or bits). By controlling the onset of cationic polymerization, the dentist has ample time to manipulate the composition while it is still in the gel form.

The invention will now be described further by way of the following examples.

EXAMPLES

Examples 1–21 and Control

A stock resin solution (Stock Solution #1) was prepared by combining 5.0 g camphorquinone (CPQ) and 15.0 g diaryliodonium hexafluoroantimonate (CD1012 from Sartomer) with 720.0 g Cyracure™ UVR 6105 cycloaliphatic diepoxide resin (available from Union Carbide), 180.0 g of a polytetrahydrofuran diol having an average molecular weight of 250 (p-THF-250, available from Aldrich Chemical Co.), and 100 g of acrylate oligomer (Ebecryl 1830, available from UCB Radcure, Inc.)), and stirring until homogeneous under safe light conditions.

A second stock solution (Stock Solution #2) was prepared by combining 10.0 g of Stock Solution #1 with a sufficient amount of a cationic polymerization modifier to achieve a modifier concentration of $1.13 \times 10^{-4}$ moles per 10.0 g of Stock Solution #1. A total of 22 solutions were prepared, each with a different cationic polymerization modifier. The following cationic polymerization modifiers were used:

| Example | Modifier |
| --- | --- |
| 1 | 4-(dimethylamino)phenylacetic acid |
| 2 | Dimethylaminphenethanol |
| 3 | Dihydroxy-p-toluidine |
| 4 | N-(3,5-dimethylphenyl)-N,N-diethanolamine |
| 5 | 2,4,6-pentamethylaniline |
| 6 | Dimethylbenzylamine |
| 7 | N,N-dimethylacetamide |
| 8 | Tetramethylurea |
| 9 | N-methyldiethanolamine |
| 10 | Triethylamine |
| 11 | 2-(methylamino)ethanol |
| 12 | Dibutylamine |
| 13 | Diethanolamine |
| 14 | N-ethylmorpholine |
| 15 | Trimethyl-1,3-propanediamine |
| 16 | 3-quinuclidinol |
| 17 | Triphenylphosphine |
| 18 | Sodium toluene sulfinate |
| 19 | Tricyclohexylphosphine |
| 20 | N-methylpyrollidone |
| 21 | T-butyldimethylaniline |

Three experimental samples were then prepared for each cationic polymerization modifier by combining sufficient amounts of Stock Solution #1 and Stock Solution #2 to arrive at samples having a modifier concentration of $1.4 \times 10^{-6}$ moles/g (prepared by combining 3.5 g of Stock Solution #1 and 0.5 g of Stock Solution #2), $2.8 \times 10^{-6}$ moles/g (prepared by combining 3.0 g of Stock Solution #1 and 1.0 g of Stock Solution #2), and $5.6 \times 10^{-6}$ moles/g (prepared by combining 2.0 g of Stock Solution #1 and #2.0), g of Stock Solution #2), respectively. A control sample was also prepared that consisted of 100% of Stock Solution #1.

The polymerization behavior of each sample was examined using differential scanning photocalorimetry ("Photo DSC"). The equipment used was a TA instruments Dual Sample Photo DSC model 2920 with a 10 mg cured resin reference. The light source was a mercury/argon lamp with an Oriel PN 59480 425 nm long pass light filter. The light intensity was 3mW/cm$^2$, measured using an International Light light meter Model IL 1400 equipped with a Model XRL, 340A detector.

An aluminum sample pan was prepared using 10 mg of each sample. The sample temperature was then raised to 37° C. and held at that temperature for one minute. Next, the light aperture was opened to irradiate the sample. During irradiation the next sample temperature was held at 37° C. The total irradiation time was 30 minutes. After 30 minutes, the aperture was closed and the sample maintained at 37° C. for one additional minute.

Data was collected as heat output per unit weight (mW/g). The data was analyzed using TA Thermal Solutions Universal Analysis software. The following parameters were determined for each sample:

$T_1$ (induction period for acrylate initiation);
$T_3$ (induction period for epoxy initiation);
$T_4$ (time to reach peak max for epoxy polymerization);
Exotherm associated with epoxy polymerization (J/g).

Photo DSC analysis was also performed on the control sample which lacked a cationic polymerization modifier. The induction period for epoxy initiation was measured and designated $T_2$. The value of $T_2$ was 1.93 minutes. The difference between $T_2$ and $T_3$ was then calculated for each sample prepared with a cationic polymerization modifier to determine the effect of the modifier on extending the epoxy induction period.

The exotherm of the control sample was determined as well. Its value was 227.9 J/g. It was then compared to the exotherm of the cationic polymerization modifier-containing samples. If the exotherm value of the modifier-containing sample was at least 5% of the exotherm value of the control sample, the epoxy polymerization was determined to be a successful polymerization.

The results of these experiments are shown in Table I. All modifier concentrations are given as moles of modifier $\times 10^{-6}$/g resin. All induction period values are given in minutes. All exotherm values are given in J/g.

The asterisks associated with Example 4 (modifier concentration=$5.6 \times 10^{-6}$ moles/g resin) and Example 20 (modifier concentration=$5.6 \times 10^{-6}$ moles/g resin) reflect the fact that the peak max for epoxy polymerization was not observed within the time scale used for the experiment (i.e., 30 minutes). With respect to the remaining samples, the results demonstrate that, with two exceptions (Example 7/modifier concentration=$1.4 \times 10^{-6}$ moles/g resin and Example 8/modifier concentration=$1.4 \times 10^{-6}$ moles/g resin), each cationic polymerization initiator, at the concentrations tested, extended the time period for cationic epoxy initiation, as evidenced by the fact that all values of $T_3$ were greater than $T_2$, without unacceptably suppressing the epoxy polymerization reaction, as evidenced by the fact that the exotherm value for each sample was greater than 5% of the corresponding value for the control sample. The relatively low $T_3$ values for the Example 7 and Example 8 samples noted above reflect the fact that epoxy initiation occurred relatively soon after acrylate initiation. However, the $T_4$-$T_3$ values, computed for these two samples as discussed below, demonstrate that, once initiated, the epoxy polymerization rate was relatively slow.

The difference between $T_4$ and $T_3$ reflects the rate at which the epoxy polymerization proceeds. The smaller the difference, the higher the polymerization rate. This difference was determined for both the modifier-containing samples and the control sample. In the case of the latter, the difference between $T_4$ and $T_2$ was determined and found to be 4.86. As shown in Table I, some of the samples exhibited differences that were less than the difference exhibited by the control sample, indicating that once initiated, the epoxy polymerization of these samples proceeded at a greater rate than that of the control sample.

TABLE I

| Example | Modifier concentration | $T_1$ | $T_3$ | $T_4$ | $T_3$-$T_2$ | $T_4$-$T_3$ | Exotherm | Exotherm/ Exotherm (control) |
|---|---|---|---|---|---|---|---|---|
| 1 | 1.4 | 0.08 | 2.50 | 6.22 | 0.57 | 3.72 | 220.6 | 0.97 |
|   | 2.8 | 0.07 | 3.29 | 7.07 | 1.36 | 3.78 | 220.2 | 0.97 |
|   | 5.6 | 0.05 | 4.74 | 9.74 | 2.81 | 5.00 | 246.6 | 1.08 |
| 2 | 1.4 | 0.08 | 2.92 | 6.79 | 0.99 | 3.87 | 225.2 | 0.99 |
|   | 2.8 | 0.09 | 4.14 | 7.99 | 2.21 | 3.85 | 220.9 | 0.97 |
|   | 5.6 | 0.09 | 6.13 | 10.83 | 4.20 | 4.70 | 241.0 | 1.06 |
| 3 | 1.4 | 0.06 | 7.25 | 12.45 | 5.32 | 5.2 | 228.8 | 1.0 |
|   | 2.8 | 0.07 | 11.01 | 16.83 | 9.08 | 5.82 | 193.4 | 0.85 |
|   | 5.6 | 0.06 | 18.91 | 26.61 | 16.98 | 7.7 | 74.6 | 0.33 |
| 4 | 1.4 | 0.15 | 7.68 | 13.89 | 5.75 | 6.21 | 200.5 | 0.88 |
|   | 2.8 | 0.18 | 11.61 | 19.19 | 9.68 | 7.58 | 168.9 | 0.74 |
|   | 5.6 | 0.20 | * | * | * | * | * | * |
| 5 | 1.4 | 0.06 | 2.62 | 6.70 | 0.69 | 4.08 | 235.7 | 1.03 |
|   | 2.8 | 0.05 | 3.35 | 6.76 | 1.42 | 3.41 | 232.2 | 1.02 |
|   | 5.6 | 0.04 | 5.39 | 8.98 | 3.46 | 3.59 | 230.0 | 1.01 |
| 6 | 1.4 | 0.05 | 2.15 | 5.56 | 0.22 | 3.41 | 245.9 | 1.08 |
|   | 2.8 | 0.06 | 2.52 | 5.45 | 0.59 | 2.93 | 249.1 | 1.09 |
|   | 5.6 | 0.07 | 3.19 | 6.41 | 1.26 | 3.22 | 265.1 | 1.16 |
| 7 | 1.4 | 0.08 | 1.71 | 16.30 | −0.22 | 14.59 | 155.7 | 0.68 |
|   | 2.8 | 0.08 | 9.59 | 23.28 | 7.66 | 13.69 | 88.9 | 0.39 |
|   | 5.6 | 0.11 | 13.19 | 30.01 | 11.26 | 16.82 | 50.9 | 0.22 |
| 8 | 1.4 | 0.12 | 1.90 | 13.72 | −0.03 | 11.82 | 163.0 | 0.71 |
|   | 2.8 | 0.14 | 1.99 | 19.24 | 0.06 | 17.25 | 111.1 | 0.49 |
|   | 5.6 | 0.11 | 1.95 | 30.01 | 0.02 | 28.06 | 61.5 | 0.27 |
| 9 | 1.4 | 0.10 | 2.73 | 5.25 | 0.8 | 2.52 | 269.4 | 1.18 |
|   | 2.8 | 0.11 | 3.31 | 5.51 | 1.38 | 2.2 | 269.9 | 1.18 |
|   | 5.6 | 0.13 | 4.55 | 6.85 | 2.62 | 2.3 | 269.0 | 1.18 |
| 10 | 1.4 | 0.16 | 2.99 | 5.50 | 1.06 | 2.51 | 281.6 | 1.23 |
|   | 2.8 | 0.17 | 3.66 | 5.75 | 1.73 | 2.09 | 277.5 | 1.22 |
|   | 5.6 | 0.11 | 4.75 | 6.66 | 2.82 | 1.91 | 285.1 | 1.25 |
| 11 | 1.4 | 0.10 | 2.99 | 5.57 | 1.06 | 2.58 | 278.5 | 1.22 |
|   | 2.8 | 0.10 | 3.77 | 5.83 | 1.84 | 2.06 | 280.2 | 1.23 |
|   | 5.6 | 0.12 | 5.63 | 7.61 | 3.70 | 1.98 | 282.8 | 1.24 |
| 12 | 1.4 | 0.05 | 2.55 | 4.94 | 0.62 | 2.39 | 281.5 | 1.23 |
|   | 2.8 | 0.05 | 3.33 | 5.26 | 1.4 | 1.93 | 275.8 | 1.21 |
|   | 5.6 | 0.05 | 5.09 | 7.01 | 3.16 | 1.92 | 286.2 | 1.25 |
| 13 | 1.4 | 0.06 | 2.44 | 4.94 | 0.51 | 2.5 | 272.0 | 1.19 |
|   | 2.8 | 0.07 | 3.02 | 5.02 | 1.09 | 2.0 | 270.4 | 1.19 |
|   | 5.6 | 0.08 | 4.19 | 6.02 | 2.26 | 1.83 | 274.6 | 1.20 |
| 14 | 1.4 | 0.08 | 2.41 | 5.09 | 0.48 | 2.68 | 278.6 | 1.22 |
|   | 2.8 | 0.08 | 2.82 | 5.36 | 0.89 | 2.54 | 286.4 | 1.26 |
|   | 5.6 | 0.07 | 3.62 | 6.30 | 1.69 | 2.68 | 274.5 | 1.20 |
| 15 | 1.4 | 0.05 | 3.23 | 5.48 | 1.3 | 2.25 | 268.1 | 1.18 |
|   | 2.8 | 0.07 | 4.73 | 7.01 | 2.8 | 2.28 | 257.1 | 1.13 |
|   | 5.6 | 0.06 | 8.21 | 11.88 | 6.28 | 3.67 | 235.2 | 1.03 |
| 16 | 1.4 | 0.06 | 2.39 | 4.84 | 0.46 | 2.45 | 262.7 | 1.15 |
|   | 2.8 | 0.07 | 3.22 | 5.22 | 1.29 | 2.0 | 260.0 | 1.14 |
|   | 5.6 | 0.06 | 4.87 | 6.78 | 2.94 | 1.91 | 266.4 | 1.17 |
| 17 | 1.4 | 0.08 | 1.95 | 11.81 | 0.02 | 9.86 | 220.3 | 0.97 |
|   | 2.8 | 0.08 | 2.69 | 15.62 | 0.76 | 12.93 | 186.3 | 0.82 |
|   | 5.6 | 0.07 | 5.21 | 19.38 | 3.28 | 14.17 | 154.8 | 0.68 |
| 18 | 1.4 | 0.10 | 2.20 | 5.51 | 0.27 | 3.31 | 264.7 | 1.16 |
|   | 2.8 | 0.10 | 2.65 | 5.51 | 0.72 | 2.86 | 256.0 | 1.12 |
|   | 5.6 | 0.08 | 3.41 | 5.79 | 1.48 | 2.38 | 274.2 | 1.20 |
| 19 | 1.4 | 0.07 | 4.51 | 10.95 | 2.58 | 6.44 | 226.6 | 0.99 |
|   | 2.8 | 0.08 | 7.02 | 14.99 | 5.09 | 7.97 | 189.3 | 0.83 |
|   | 5.6 | 0.09 | 11.15 | 21.27 | 9.22 | 10.12 | 131.5 | 0.58 |
| 20 | 1.4 | 0.10 | 7.96 | 16.26 | 6.03 | 8.3 | 187.0 | 0.82 |
|   | 2.8 | 0.11 | 14.14 | 24.15 | 12.21 | 10.01 | 92.2 | 0.40 |
|   | 5.6 | 0.09 | * | * | * | * | * | * |
| 21 | 1.4 | 0.08 | 2.81 | 6.30 | 0.88 | 3.49 | 246.9 | 1.08 |
|   | 2.8 | 0.08 | 3.96 | 7.68 | 2.03 | 3.72 | 247.4 | 1.08 |
|   | 5.6 | 0.07 | 5.60 | 10.12 | 3.67 | 4.52 | 257.2 | 1.13 |

Examples 22–24 and Control

The procedure of Examples 1–21 was followed except that filled composite samples were tested. In addition, a stock solution (Stock Solution #3) having modifier concentrations two times higher than the amounts used in Stock Solution #2 were used to prepare samples for testing. Three different modifiers were tested: 2-(methylamino)ethanol (Example 22), trimethyl-1,3-propanediamine (Example 23), and t-butyldimethyl aniline (Example 24). Four experimental samples were then prepared for each cationic polymerization modifier by combining sufficient amounts of Stock Solution #1 and Stock Solution #3 to arrive at samples having a modifier concentration of $2.8\times10^{-6}$ moles/g (prepared by combining 3.5 g of Stock Solution #1 and 0.5 g of Stock Solution #2), $5.6\times10^{-6}$ moles/g (prepared by combining 3.0 g of Stock Solution #1 and 1.0 g of Stock Solution #2), $11.26\times10^{-6}$ moles/g (prepared by combining 2.0 g of Stock Solution #1 and 2.0 g of Stock Solution #2), and $22.4\times10^{-6}$ moles/g (prepared by combining 0.0 g of Stock Solution #1 and 4.0 g of Stock Solution #2), respectively. A control sample was also prepared that consisted of 100% of Stock Solution #1. Each sample, including the control sample, was then combined with a sufficient amount of an epoxy silane-treated quartz filler to create a filled paste having 84% by weight filler and 16% by weight resin.

The samples were then subjected to Photo DSC as described above. The results are reported in Table II. The designation "###" means that no measurable epoxy polymerization could be detected within the time period of the test (i.e., 30 minutes), suggesting that the modifier concentration was so high that it suppressed epoxy polymerization, rather than merely delaying it. For comparison purposes, the control sample exhibited a $T_2$, value of 2.99, a $T_4$ value of 6.37, and an exotherm value of 58.99 J/g. The difference between $T_4$ and $T_2$, reflecting the rate of polymerization for the control sample, was 3.38.

The results shown in Table II demonstrate that both the identity of the modifier and its concentration are important with respect to the ability of the modifier to delay the onset of epoxy polymerization without suppressing polymerization entirely.

modifier concentration ($22.4\times10^{-6}$ moles/g resin). Acrylate polymerization initiation occurred first. The induction period for acrylate polymerization was short and relatively unchanged regardless of the modifier concentration. However, at modifier concentrations of $5.6\times10^{-6}$ moles/g resin and $11.2\times10^{-6}$ moles/g resin, the epoxy induction period was clearly lengthened relative to the control sample. In each case, however, epoxy polymerization proceeded successfully once initiated. Moreover, the rate of epoxy polymerization was greater than the rate of the control sample, as evidenced by the fact that the epoxy exotherm peak was narrower for the modifier-containing samples relative to the control sample; the effect was particularly pronounced in the case of the sample containing $5.6\times10^{-6}$ moles/g resin. Once the modifier concentration reached $22.4\times10^{-6}$ g/mole resin, however, the epoxy polymerization was suppressed, as evidenced by the lack of a detectable epoxy peak.

Figure 2:
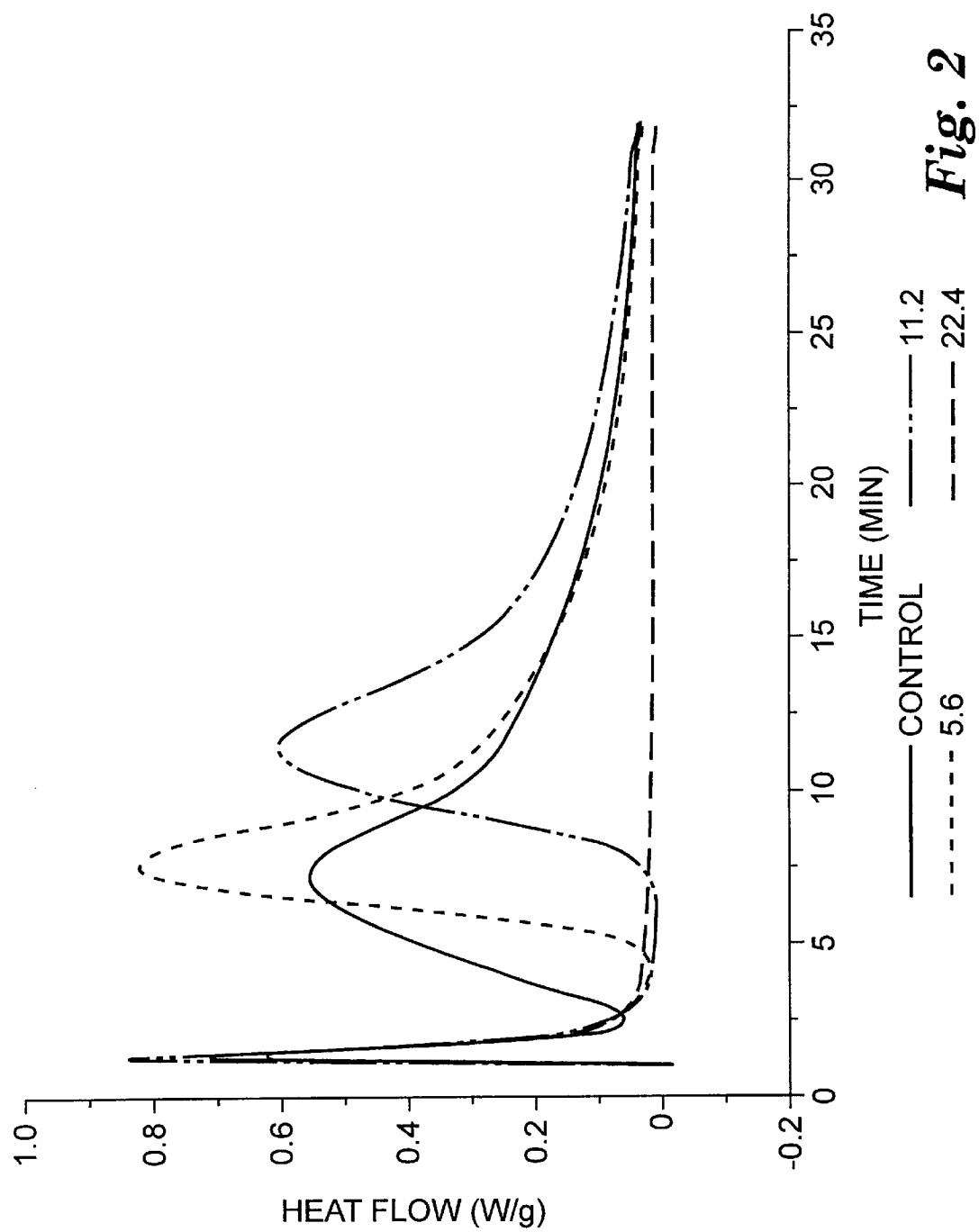
FIG. 2 is a plot of heat flow vs. time obtained by Photo Differential Scanning Calorimetry for polymerizable compositions containing various concentrations of the cationic polymerization modifier N,N,N'-trimethyl-1,3-propanediamine.

Similar effects were observed in FIG. 2 in the case of Example 26. Samples containing $2.8\times10^{-6}$ g/mole resin and $5.6\times10^{-6}$ g/mole resin exhibited longer induction periods for epoxy polymerization relative to the control sample, while acrylate polymerization was relatively unaffected. The $2.8\times10^{-6}$ g/mole resin sample also exhibited a higher epoxy polymerization rate than the control sample, as evidenced by the narrower peak. At a modifier concentration of $11.2\times10{-6}$ g/mole resin, the epoxy polymerization was suppressed, as evidenced by the lack of a detectable epoxy peak.

Examples 27–30

These examples describe epoxy-acrylate blends polymerized using a dual irradiation procedure.

TABLE II

| Example | Modifier concentration | $T_1$ | $T_3$ | $T_4$ | $T_3-T_2$ | $T_4-T_3$ | Exotherm | Exotherm/ Exotherm (control) |
|---|---|---|---|---|---|---|---|---|
| 22 | 2.8 | 0.03 | 2.89 | 6.20 | −0.1 | 3.31 | 52.97 | 0.90 |
|  | 5.6 | 0.04 | 3.50 | 6.61 | 0.51 | 3.11 | 61.15 | 1.04 |
|  | 11.2 | 0.02 | 5.41 | 9.96 | 2.42 | 4.55 | 51.99 | 0.88 |
|  | 22.4 | 0.03 | 9.77 | 20.38 | 6.78 | 10.61 | 9.51 | 0.16 |
| 23 | 2.8 | 0.04 | 4.17 | 7.37 | 1.18 | 3.2 | 53.32 | 0.90 |
|  | 5.6 | 0.04 | 6.62 | 11.15 | 3.63 | 4.53 | 54.08 | 0.92 |
|  | 11.2 | 0.04 | ### | ### | ### | ### | ### | ### |
|  | 22.4 | 0.05 | ### | ### | ### | ### | ### | ### |
| 24 | 2.8 | 0.06 | 2.63 | 6.77 | −0.36 | 4.14 | 50.51 | 0.86 |
|  | 5.6 | 0.05 | 3.15 | 7.45 | 0.16 | 4.3 | 59.41 | 1.01 |
|  | 11.2 | 0.04 | 4.49 | 9.81 | 1.50 | 5.32 | 50.75 | 0.86 |
|  | 22.4 | 0.05 | 6.19 | 15.55 | 3.2 | 9.36 | 17.95 | 0.30 |

Examples 25–26 and Control

Two sets of samples were prepared following the procedure used to prepare Examples 22–24. The first set of samples (Example 25) included three samples prepared using 2-(methylamino)-ethanol as the cationic polymerization modifier in concentrations of $5.6\times10^{-6}$ moles/g resin, $11.2\times10^{-6}$ moles/g resin, and $22.4\times10^{-6}$ moles/g resin. The second set of samples (Example 26) included three samples prepared using trimethyl-1,1,3-propanediamine as the cationic polymerization modifier in concentrations of $2.8\times10^{-6}$ moles/g resin, $5.6\times10^{-6}$ moles/g resin, and $11.2\times10^{-6}$ moles/g resin. The samples, as well as a control sample, were then subjected to Photo DSC as described above. The results are shown in FIG. 1 (Example 25) and FIG. 2 (Example 26).

Referring to FIG. 1, two distinct peaks were observed, with the exception of the sample containing the highest Four resin solutions were prepared by combining various amounts of camphorquinone (CPQ), diaryliodonium hexafluoroantimonate (CD1012), and t-butyldimethyl aniline (tBDMA) with UVR 6105 cycloaliphatic diepoxide resin (73.6 wt. %), p-THF-250 (18.4 wt. %), and Ebecryl 1830 acrylate oligomer (8 wt. %), and stirring until homogeneous under safe light conditions. The amounts of CPQ, CD1012, and tBDMA for each example were as follows (all amounts in wt. %):

| Example | CPQ | CD1012 | TBDMA |
|---|---|---|---|
| 27 | 0.7 | 1.0 | 0.2 |
| 28 | 0.7 | 2.0 | 0.2 |

-continued

| Example | CPQ | CD1012 | TBDMA |
|---------|-----|--------|-------|
| 29 | 0.2 | 1.0 | 0.2 |
| 30 | 0.2 | 2.0 | 0.2 |

Each sample was placed on a polyester film and then irradiated using a 3M Model 5530 AAWZ curing light having a 12 mm light guide. The distance between the curing light and the sample was 1 cm. Each sample was irradiated for 10 seconds and then tested for handling characteristics. Each sample was then allowed to sit for 5 minutes and then re-evaluated, after which each sample was irradiated until it formed a hard solid. All samples remained relatively soft and manipulatable after periods of 10 seconds and 5 minutes following the first irradiation, and formed hard solids following the second irradiation.

Example 31

This example describes polymerization of an epoxy/methacrylate composition using a redox initiation system (benzoyl peroxide plus dimethylaminphenethanol ("DMAPE")) for initiating free radical polymerization of the acrylate and an iodonium salt for initiating cationic polymerization of the epoxy.

A stock solution ("Stock Solution #4") was prepared by combining 0.1 g camphorquinone (CPQ), 0.3 g diaryliodonium hexafluoroantimonate (CD1012), 18.0 g UVR 6105 cycloaliphatic diepoxide resin, and 2 g Ebecryl 1830 acrylate oligomer with stirring until homogeneous under safe light conditions. 9.94 g of Stock Solution #4 was then combined with 0.03 g ethyl dimethylaminobenzoate ("EDMAB") and 0.03 g DMAPE to create Stock Solution #5. An additional 9.90 g of Stock Solution #4 was combined with 0.10 g benzoyl peroxide to create Stock Solution #6.

0.50 mL of Stock Solution #5 and 0.50 mL of Stock Solution #6 were combined in a glass vial and mixed thoroughly in a dark room. After 7.5 minutes, the mass had solidified to form a gelatinous solid, reflecting polymerization of the Ebecryl 1830 acrylate oligomer. The gelled material was then exposed to light from a 3M Visilux 2 dental curing light commercially available from 3M Company of St. Paul, Minn. to initiate epoxy polymerization. After a 50 second exposure the material exothermed and formed a hard solid.

In a second experiment, the gelled material was not exposed to the Visilux light. In the absence of exposure, the material remained gelled (i.e., it did not form a hard solid) for an extended period of time, reflecting the absence of any measurable epoxy polymerization.

Other embodiments are within the following claims.

For Example, the above-described polymerizable compositions may be provided on a substrate.

What is claimed is:

1. A photopolymerizable dental composition comprising:
   (a) a cationically active functional group;
   (b) a free radically active functional group; and
   (c) a photoinitiation system capable of initiating, at a reaction temperature less than about 40° C., free radical polymerization of said free radically active functional group after a finite induction period $T_1$ and cationic polymerization of said cationically active functional group after a finite induction period $T_3$, where $T_3$ is greater than $T_1$, said photoinitiation system comprising:
   (i) a source of species capable of initiating free radical polymerization of said free radically active functional group and cationic polymerization of said cationically active functional group; and
   (ii) a cationic polymerization modifier,
wherein in the absence of said modifier, cationic polymerization of said cationically active functional group is initiated under the same irradiation conditions at the end of a finite induction period $T_2$, where $T_2$ is less than $T_3$.

2. A photopolymerizable composition according to claim 1 wherein said source comprises an onium salt.

3. A photopolymerizable composition according to claim 1 wherein said source comprises an iodonium salt.

4. A photopolymerizable composition according to claim 1 wherein cationic polymerization of said cationically active functional group after a finite induction period $T_3$ proceeds at a rate that is greater than the rate in the absence of said cationic polymerization modifier under the same irradiation conditions.

5. A photopolymerizable composition according to claim 1 wherein said photoinitiator system has a photoinduced potential less than that of 3-dimethylaminobenzoic acid in a standard solution of $2.9 \times 10^{-5}$ moles/g diphenyliodonium hexafluoroantimonate and $1.5 \times 10^{-5}$ moles/g camphorquinone in 2-butanone.

6. A photopolymerizable composition according to claim 1 wherein said modifier has a $pk_b$ value measured in aqueous solution of no greater than 10.

7. A photopolymerizable composition according to claim 1 wherein said modifier comprises an aromatic amine.

8. A photopolymerizable composition according to claim 7 wherein said aromatic amine comprises t-butyldimethylaniline.

9. A photopolymerizable composition according to claim 1 wherein said modifier comprises an aliphatic amine.

10. A photopolymerizable composition according to claim 9 wherein said aliphatic amine is selected from the group consisting of trimethyl-1,3-propane diamine, 2-(methylamino)ethanol, and combinations thereof.

11. A photopolymerizable composition according to claim 1 wherein said modifier comprises an aliphatic amide.

12. A photopolymerizable composition according to claim 1 wherein said modifier comprises an aliphatic urea.

13. A photopolymerizable composition according to claim 1 wherein said modifier comprises a phosphine.

14. A photopolymerizable composition according to claim 1 wherein said modifier comprises a salt of an organic or inorganic acid.

15. A photopolymerizable composition according to claim 14 wherein said modifier comprises a sulfinic acid salt.

16. A photopolymerizable composition according to claim 1 wherein said photoinitiation system further comprises a photosensitizer.

17. A photopolymerizable composition according to claim 16 wherein said photosensitizer comprises a visible light sensitizer.

18. A photopolymerizable composition according to claim 16 wherein said photosensitizer comprises an alpha diketone.

19. A photopolymerizable composition according to claim 1 wherein said composition comprises an epoxy resin having a cationically active functional group.

20. A photopolymerizable composition according to claim 1 wherein said composition comprises a vinyl ether having a cationically active functional group.

21. A photopolymerizable composition according to claim 1 wherein said composition comprises an ethylenically unsaturated compound having a free radically active functional group.

22. A photopolymerizable composition according to claim 21 wherein said ethylenically unsaturated compound is selected from the group consisting of an acrylic acid ester, a methacrylic acid ester, and combinations thereof.

23. A photopolymerizable composition according to claim 21 wherein said ethylenically unsaturated compound is selected from the group consisting of a hydroxy-functional acrylic acid ester, a hydroxy-functional methacrylic acid ester, and combinations thereof.

24. A photopolymerizable composition according to claim 1 wherein said composition comprises (a) an epoxy resin having a cationically active functional group and (b) ethylenically unsaturated compound having a free radically active functional group selected from the group consisting of an acrylic acid ester, a methacrylic acid ester, and combinations thereof.

25. A photopolymerizable composition according to claim 1 wherein said composition comprises (a) a vinyl ether resin having a cationically active functional group and (b) ethylenically unsaturated compound having a free radically active functional group selected from the group consisting of an acrylic acid ester, a methacrylic acid ester, and combinations thereof.

26. A photopolymerizable composition according to claim 1 wherein said composition comprises a polymerizable component comprising a cationically active functional group and a free radically active functional group.

27. A photopolymerizable composition according to claim 26 wherein said polymerizable component is selected from the group consisting of an epoxy-functional acrylic acid ester, an epoxy-functional methacrylic acid ester, and combinations thereof.

28. A photopolymerizable composition according to claim 1 further comprising a polyol.

29. A dental adhesive comprising a photopolymerizable composition according to claim 1.

30. A dental composite comprising a photopolymerizable composition according to claim 1.

31. A dental sealant comprising a photopolymerizable composition according to claim 1.

32. A photopolymerizable composition comprising:
(a) a cationically active functional group;
(b) a free radically active functional group; and
(c) a photoinitiation system capable of initiating, at a reaction temperature less than about 40° C., free radical polymerization of said free radically active functional group after a finite induction period $T_1$ and cationic polymerization of said cationically active functional group after a finite induction period $T_3$, where $T_3$ is greater than $T_1$,
said photoinitiation system comprising:
(i) a source of species capable of initiating free radical polymerization of said free radically active functional group and cationic polymerization of said cationically active functional group; and
(ii) a cationic polymerization modifier,
wherein in the absence of said modifier, cationic polymerization of said cationically active functional group is initiated under the same irradiation conditions at the end of a finite induction period $T_2$, where $T_2$ is less than $T_3$.

33. A method of polymerizing a photopolymerizable dental composition, said method comprising applying said composition to a surface and exposing said composition to a source of actinic radiation at a reaction temperature less than 40° C.,
said photopolymerizable composition comprising:
(a) a cationically active functional group;
(b) a free radically active functional group; and
(c) a photoinitiation system capable of initiating, at said reaction temperature, free radical polymerization of said free radically active functional group after a finite induction period $T_1$ and cationic polymerization of said cationically active functional group after a finite induction period $T_3$, where $T_3$ is greater than $T_1$,
said photoinitiation system comprising:
(i) a source of species capable of initiating free radical polymerization of said free radically active functional group and cationic polymerization of said cationically active functional group; and
(ii) a cationic polymerization modifier,
wherein in the absence of said modifier, cationic polymerization of said cationically active functional group is initiated under the same irradiation conditions at the end of a finite induction period $T_2$, where $T_2$ is less than $T_3$.

34. A method according to claim 33 comprising continuously exposing said photopolymerizable composition to a source of actinic radiation.

35. A method according to claim 33 comprising exposing said photopolymerizable composition to a single dose of actinic radiation.

36. A method according to claim 33 comprising:
(a) exposing said photopolymerizable composition at a first reaction temperature to a first dose of actinic radiation to initiate polymerization of said free radically active functional group after a finite induction period $T_1$; and
(b) thereafter exposing said photopolymerizable composition at a second reaction temperature to a second dose of actinic radiation to initiate polymerization of said cationically active functional group after a finite induction period $T_3$.

37. A method according to claim 36 wherein said actinic radiation of said first dose has the same wavelength as said actinic radiation of said second dose.

38. A method according to claim 33 wherein said actinic radiation comprises visible radiation.

39. A method according to claim 33 wherein said photopolymerizable composition comprises an epoxy resin having a cationically active functional group.

40. A method according to claim 33 wherein said photopolymerizable composition comprises (a) an epoxy resin having a cationically active functional group and (b) an ethylenically unsaturated compound having a free radically active functional group selected from the group consisting of an acrylic acid ester, a methacrylic acid ester, and combinations thereof.

41. A method according to claim 33 wherein said photopolymerizable composition comprises a polymerizable component comprising a cationically active functional group and a free radically active functional group.

42. A method according to claim 36 wherein said first reaction temperature and said second reaction temperature are substantially the same.

43. A method of polymerizing a composition, said method comprising exposing a photopolymerizable composition to a source of actinic radiation at a reaction temperature, said photopolymerizable composition comprising:
- (a) a cationically active functional group;
- (b) a free radically active functional group; and
- (c) a photoinitiation system capable of initiating, at said reaction temperature, free radical polymerization of said free radically active functional group after a finite induction period $T_1$ and cationic polymerization of said cationically active functional group after a finite induction period $T_3$, where $T_3$ is greater than $T_1$, said photoinitiation system comprising:
- (i) a source of species capable of initiating free radical polymerization of said free radically active functional group and cationic polymerization of said cationically active functional group; and
- (ii) a cationic polymerization modifier, wherein in the absence of said modifier, cationic polymerization of said cationically active functional group is initiated under the same irradiation conditions at the end of a finite induction period $T_2$, where $T_2$ is less than $T_3$.

44. A method of preparing a polymerized dental composition, said method comprising:
- (a) providing a polymerizable dental composition comprising:
  - (i) a cationically active functional group;
  - (ii) a free radically active functional group;
  - (iii) a first initiation system capable of initiating free radical polymerization of said free radically active functional group at a first reaction temperature less than 40° C,; and
  - (iv) a second initiation system different from said first initiation system that is capable of initiating photo-induced cationic polymerization of said cationically active functional group at a second reaction temperature less than 40° C.;
- (b) applying said composition to a surface,
- (c) inducing polymerization of said free radically active functional group at said first reaction temperature; and
- (d) thereafter exposing said composition to actinic radiation at said second reaction temperature to cause polymerization of said cationically active functional group.

45. A method according to claim 44 wherein said first initiation system comprises a photoinitiation system.

46. A method according to claim 44 wherein said first initiation system comprises a thermal initiation system.

47. A method according to claim 44 wherein said first initiation system comprises a redox initiation system.

48. A method according to claim 44 wherein said composition comprises an epoxy resin having a cationically active functional group.

49. A method according to claim 44 wherein said composition comprises (a) an epoxy resin having a cationically active functional group and (b) an ethylenically unsaturated compound having a free radically active functional group selected from the group consisting of an acrylic acid ester, a methacrylic acid ester, and combinations thereof.

50. A method according to claim 44 wherein said composition comprises a polymerizable component comprising a cationically active functional group and a free radically active functional group.

51. A method according to claim 48 wherein said first reaction temperature and said second reaction temperature are substantially the same.

52. A method of delaying the onset of cationic polymerization in a polymerizable hybrid composition, said method comprising the steps of:
- (a) providing a photopolymerizable composition comprising:
  - (i) a cationically active functional group;
  - (ii) a free radically active functional group; and
  - (iii) a photoinitiation system comprising:
    - (1) a source of species capable of initiating free radical polymerization of said free radically active functional group and cationic polymerization of said cationically active functional group; and
    - (2) a cationic polymerization modifier; and
- (b) exposing said photopolymerizable composition to a source of actinic radiation at a reaction temperature;
  wherein said photoinitiation system is capable of initiating at said reaction temperature free radical polymerization of said free radically active functional group after a finite induction period $T_1$ and cationic polymerization of said cationically active functional group after a finite induction period $T_3$, where $T_3$ is greater than $T_1$; and
  further wherein in the absence of said cationic polymerization modifier, cationic polymerization of said cationically active functional group is initiated under the same irradiation conditions at the end of a finite induction period $T_2$, where $T_2$ is less than $T_3$.

53. A method according to claim 52 wherein said reaction temperature is less than about 40° C.

54. A method according to claim 52 wherein said photopolymerizable hybrid composition is a dental composition.

55. A method according to claim 54 wherein dental composition is exposed to actinic radiation in an oral environment.

56. A method according to claim 52 comprising continuously exposing said photopolymerizable hybrid composition to a source of actinic radiation.

57. A method according to claim 52 comprising exposing said photopolymerizable hybrid composition to a single dose of actinic radiation.

58. A method according to claim 52 comprising:
- (a) exposing said photopolymerizable hybrid composition at a first reaction temperature to a first dose of actinic radiation to initiate polymerization of said free radically active functional group after a finite induction period $T_1$; and
- (b) thereafter exposing said photopolymerizable composition at a second reaction temperature to a second dose of actinic radiation to initiate polymerization of said cationically active functional group after a finite induction period $T_3$.

59. A method according to claim 52 wherein said photopolymerizable hybrid composition comprises:
- (a) an epoxy resin having a cationically active functional group; and
- (b) an ethylenically unsaturated compound having a free radically active functional group selected from the group consisting of an acrylic acid ester, a methacrylic acid ester and combinations thereof.

* * * * *